United States Patent
Nonnenmann et al.

(10) Patent No.: US 7,883,495 B2
(45) Date of Patent: Feb. 8, 2011

(54) DISPOSABLE ABSORBENT ARTICLE AND POLYMER FILM HAVING ODOR CONTROL AND/OR SKIN HEALTH AGENTS

(75) Inventors: Heather R. Nonnenmann, Warminster, PA (US); Kelly Thornton, Bensalem, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 875 days.

(21) Appl. No.: 11/805,642

(22) Filed: May 24, 2007

(65) Prior Publication Data

US 2008/0294131 A1    Nov. 27, 2008

(51) Int. Cl.
*A61F 13/15* (2006.01)
*A61F 13/20* (2006.01)

(52) U.S. Cl. .............. 604/289; 604/290; 604/359; 604/360

(58) Field of Classification Search ......... 604/359–361, 604/289, 290; 442/414
See application file for complete search history.

(56) References Cited

U.S. PATENT DOCUMENTS

| | | |
|---|---|---|
| 5,760,118 A | 6/1998 | Sinclair et al. |
| 6,433,243 B1* | 8/2002 | Woltman et al. ............ 604/359 |
| 2003/0181115 A1 | 9/2003 | Nagsuna et al. |
| 2004/0043049 A1* | 3/2004 | Erdman .................. 424/402 |
| 2004/0043688 A1 | 3/2004 | Soerens et al. |
| 2005/0008682 A1* | 1/2005 | Tramontana ............... 424/443 |
| 2005/0120497 A1* | 6/2005 | Lynde et al. ............ 15/104.94 |
| 2006/0015981 A1* | 1/2006 | Ammer et al. ................ 2/54 |
| 2006/0143767 A1* | 7/2006 | Yang et al. ................... 2/16 |
| 2007/0078426 A1 | 4/2007 | Kline et al. |
| 2007/0088303 A1* | 4/2007 | Olson et al. ............ 604/385.01 |

OTHER PUBLICATIONS

International Search Report, dated Dec. 5, 2008, for PCT/US08/64700.
Written Opinion of the International Search Authority, dated Dec. 5, 2008, for PCT/US08/64700.

* cited by examiner

*Primary Examiner*—Melanie J Hand
(74) *Attorney, Agent, or Firm*—Amster, Rothstein & Ebenstein LLP

(57) ABSTRACT

A disposable absorbent article with an associated polymer film that is positioned to be activated by contact with bodily fluids, wherein the polymer film can release odor control and/or skin wellness agents upon contact with such bodily fluids. The polymer film can release the odor control and/or skin wellness agents immediately, gradually over a period of time after contact with such bodily fluids, or a combination of both. The polymer film can also be used for household cleaning applications, in which the polymer film can similarly contain and subsequently release household cleaning agents upon contact with water.

29 Claims, 4 Drawing Sheets

DISPOSABLE ABSORBENT ARTICLE AND POLYMER FILM HAVING ODOR CONTROL AND/OR SKIN HEALTH AGENTS

BACKGROUND

The disposable absorbent article and polymer film having odor control and/or skin health agents described herein relates generally to disposable absorbent articles, and more particularly to a disposable absorbent article and associated polymer film which releases agents to control odor and/or provide various types of skin wellness benefits.

Disposable absorbent articles are known in the art which have odor control compositions, skin health additives, and combinations of both. See, for example, U.S. Pat. Nos. 6,369,290 (Glaug et al.) entitled "Time Release Odor Control Composition For A Disposable Article"; 6,459,014 (Chmielewski et al.) entitled "Absorbent Article Which Maintains Prolonged Natural Skin PH;" and 6,855,134 (Brooks) entitled "Disposable Absorbent Articles With Skin Health And Odor Control Additives."

Additionally, film forming polymer compositions for use as a topical agent delivery system are also known in the art. See, for example, U.S. Pat. No. 5,911,980 (Samour et al.) entitled "Lipophilic And Amphiphilic or Hydrophilic Film-Forming Polymer Compositions, And Use Thereof In Topical Agent Delivery System And Method Of Delivering Agents To The Skin."

SUMMARY

A disposable absorbent article and polymer film having odor control and/or skin health agents is described herein. The polymer film can be associated with any conventional type of disposable absorbent article. The polymer film can be positioned against or adjacent to the body of the user to be activated by contact with bodily fluids. Upon contact with bodily fluids, the polymer film can release odor control and/or skin wellness agents. The polymer film can be formulated to release the odor control and/or skin wellness agents immediately upon contact with bodily fluids, or gradually over a period of time after such contact.

The odor control agents can be various types of odor eliminating agents, and can also include fragrances (or scents). The skin wellness agents can comprise pH regulating agents, anti-fungal agents, anti-bacterial agents, anti-viral agents, anti-itch agents, an anti-inflammatory agents, lubricants, deodorants, and/or antiperspirants.

As conventionally known, disposable absorbent articles can commonly comprise a top sheet, a back sheet, and an absorbent core disposed therebetween. Additionally, conventional absorbent cores can also be known to be comprised of different components, for example, a core wrap surrounding the core, and a fluid acquisition layer between the core wrap and the top sheet. The absorbent core can be comprised of various materials, including, for example, pulp, superabsorbent polymers (SAP), tow fibers, creped cellulose wadding, absorbent foams, absorbent sponges, absorbent gelling materials, fiberized cellulose, fluff pulp having tissue or synthetic materials, and/or any equivalent material or combination of materials. The size and capacity of the absorbent material should correspond to the application, for example, an incontinent brief for an adult may require a larger absorbent core than a diaper for a child. Zoned absorbency also may be used if desired. Certain types of disposable absorbent articles are also known to further comprise leg gathers, leg cuffs, a tummy band, and/or side panels. The polymer film can be variously positioned within the disposable absorbent article with respect to any of these various components.

In further another embodiment, the polymer film comprising at least one of odor control and skin wellness agents can be adapted to be applied to, such as by an appropriate adhesive, to either a portion of the disposable absorbent article, or directly to the skin of the user. Where the polymer film were designed to contact and/or adhere to the skin of the user, the polymer film could conceivably be utilized alone, for example, as underarm deodorant and/or antiperspirant. Additionally, the polymer film could be used for shoe inserts, for example to apply odor control and/or skin wellness agents to a person's feet. In additional embodiments, the polymer film could be used with an absorbent cleaning pad for household cleaning applications.

Certain illustrative aspects of the disposable absorbent article and polymer film having odor control and/or skin wellness agents are described herein in connection with the following description and the appended drawings. These aspects may be indicative of but a few of the various ways in which the principles of the disposable absorbent article and polymer film having odor control and/or skin wellness agents may be employed, and which is intended to include all such aspects and any equivalents thereof. Other advantages and features of the disposable absorbent article and polymer film having odor control and/or skin wellness agents may become apparent from the following detailed description, when considered in conjunction with the appended drawing figures.

BRIEF DESCRIPTION OF THE DRAWING FIGURES

A more complete understanding of the disposable absorbent article and polymer film having odor control and/or skin wellness agents can be obtained by considering the following description in conjunction with the accompanying drawings, in which.

DESCRIPTION OF CERTAIN EMBODIMENTS

Disposable absorbent articles are well known in the art. A non-exhaustive list of examples of absorbent articles includes diapers, diaper covers, disposable diapers, training pants, feminine hygiene products and adult incontinence products. Moreover, although a "disposable" absorbent article is described herein, it is to be understood that such "disposable" articles may be intended to be either fully or only partially discarded after a single use. Thus, "disposable" articles can comprise a single inseparable structure, in which the entire article is disposable, or may also comprise articles having replaceable inserts or other interchangeable parts, in which only those inserts or interchangeable parts are disposable. As used herein, the terms "absorbent article," "absorbent garment," or simply "article" or "garment," refer to devices that absorb and contain body fluids and other body exudates. More specifically, these terms refer to articles that are placed against or in proximity to the body of a wearer to absorb and contain the various exudates discharged from the body.

Though different in appearance and dimensions, all of these types of articles can generally perform the same basic function of fluid absorption and retention and can all be generally based upon the same fundamental technology. Nearly all of these types of absorbent articles are comprised of a top sheet, a back sheet, and an absorbent core sandwiched between the top sheet and back sheet. The absorbent core is located within the article at a position to receive bodily fluids. Optionally, a fluid acquisition layer may also be disposed between the top sheet and the absorbent core. Although these types of articles are typically designed such that bodily fluids will preferably contact only the absorbent core, some of these articles further include leg cuffs, tummy bands, side panels, and other portions which could possibly also come into contact with bodily fluids.

The disposable absorbent article and polymer film having odor control and/or skin health agents described herein may be used with all of the foregoing classes of absorbent articles, without limitation, whether entirely disposable or otherwise.

Figure 1:
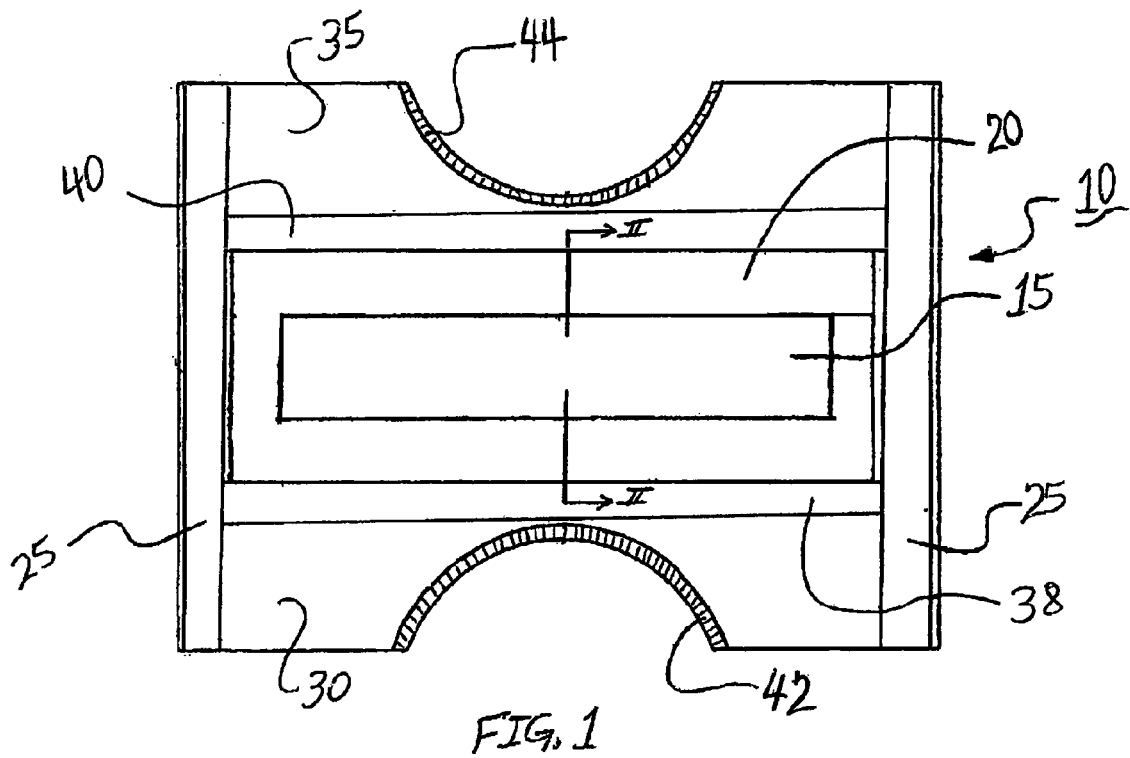
FIG. 1 is a top plan view of an embodiment of a disposable absorbent article and polymer film having odor control and/or skin wellness agents.

Referring now to the drawing figures, wherein like reference numerals are used to refer to like elements throughout, a disposable absorbent article 10 and polymer film 15 having odor control and/or skin wellness agents is illustrated in the top plan view in FIG. 1. As shown, the disposable absorbent article 10 can be of a conventional type, such as a diaper, and can generally comprise an absorbent core 20 along with a tummy band 25, side panels 30, 35, leg gathers 38, 40 and elasticized leg cuffs 42, 44.

Figure 2:
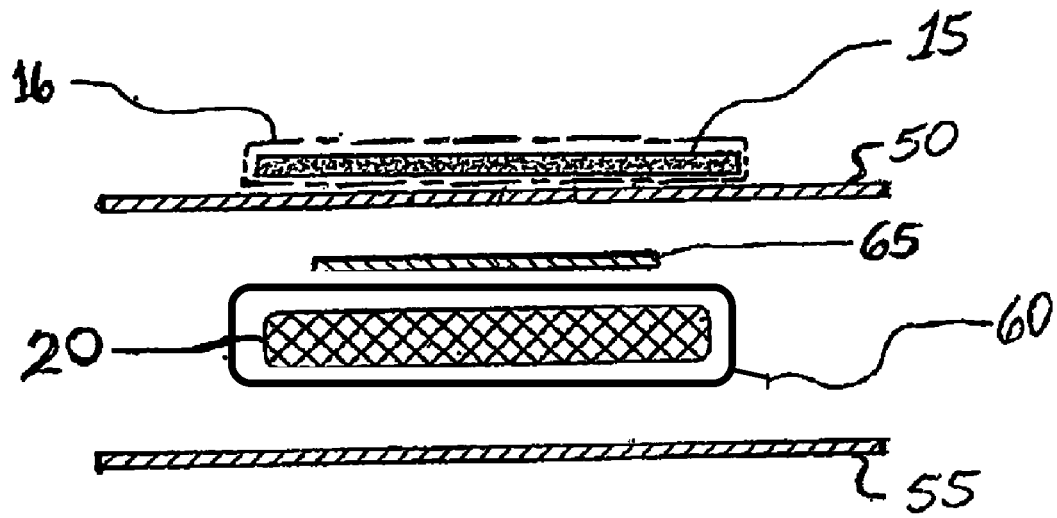
FIG. 2 is a cross section view taken along line II-II in FIG. 1.

Further details of the disposable absorbent article 10, and particularly the absorbent core 20, are illustrated in FIG. 2, which is a cross section view taken along line II-II in FIG. 1. As shown, the disposable absorbent article 10 can further comprise a top sheet 50 and a back sheet 55, between which the absorbent core 20 is conventionally disposed. Additionally, the absorbent core 20 can also be known to be comprised of multiple components, including, for example, a core wrap 60 surrounding the absorbent core 20, and a fluid acquisition layer 65 between the core wrap 60 and the top sheet 50. Although shown generally rectangular shaped, the absorbent core 20 can be differently shaped, including oval or hourglass shaped. The absorbent core 20 can be comprised of various materials, including, for example, pulp, superabsorbent polymers (SAP), tow fibers, creped cellulose wadding, absorbent foams, absorbent sponges, absorbent gelling materials, fiberized cellulose, fluff pulp having tissue or synthetic materials, and/or any equivalent material or combination of materials. The size and capacity of the absorbent material should correspond to the application, for example, an incontinent brief for an adult may require a larger absorbent core than a diaper for a child. Zoned absorbency also may be used, if desired. For example, more absorbent capacity may be located in particular regions of the disposable absorbent article 10 depending on, for example, the gender of the intended wearer or the intended use for the disposable absorbent article 10.

In FIGS. 1 and 2 the polymer film 15 is shown as being disposed on the top sheet 50. However, the polymer film 15 could alternatively be positioned variously with respect to any of the aforesaid components of the disposable absorbent article 10. In an embodiment where the polymer film 15 were disposed on top of the cover sheet 50, in some cases an optional cover sheet 16, shown in phantom lines in FIG. 2, for the polymer film 15 can be provided if direct contact between the skin and the polymer film is desired to be avoided. Reasons for doing this could include providing a more comfortable interface with the bare skin, or avoiding any possible discomfort if the user has sensitive skin. For example, the polymer film 15 may uncomfortably adhere to the skin prior to dissolution, or edges of the polymer film 15 could possibly poke or scrape the skin, or there could be various skin sensitivity reasons why a cover sheet 16 might be desired. The cover sheet 16 need not entirely surround the polymer film 15, but could simply be a single layer applied to the top surface thereof that would provide an interface between the polymer film 15 and the skin. The cover sheet 16 could be prefabricated around the polymer film 15, or could be a separate sheet, or pouch, which could be selectively used by the individual user if desired. Such a separate sheet or pouch could be designed to be adhered, or otherwise attached, to the top sheet 50 of the disposable absorbent article 10.

Although shown positioned on the top sheet 50, the polymer film 15 could alternatively be positioned between the top sheet 50 and the absorbent core 20, or between the back sheet 55 and the absorbent core 20. Additionally, the polymer film 15 could be alternatively positioned between the top sheet 50 and the fluid acquisition layer 65, between the fluid acquisition layer 65 and the core wrap 60, between the core wrap 60 and the absorbent core 20, or could even be incorporated into the absorbent core 20 itself. Furthermore, the polymer film 15 could also instead be provided on, adjacent to, or in some manner incorporated with any of the tummy band 25, side panels 30, 35, leg gathers 38, 40 and/or leg cuffs 42, 44.

In general, the polymer film 15 having odor control and/or skin health agents can be positioned within the disposable absorbent article 10 in any of a number of positions with respect to the various components thereof. In any case, the polymer film 15 would need only be operably located such that the polymer film 15 will be contacted by the discharge of bodily fluids into the disposable absorbent article 10. Upon contact with bodily fluids, the polymer film 15 will release the odor control and/or skin wellness agents. Bodily fluids can include the known types of such fluids, for example, urine, menses, blood, discharge, bowel movement, sweat, and others.

The polymer film 15 can be formulated to release the odor control and/or skin wellness agents immediately, gradually over a period of time after contact with bodily fluids, or a combination thereof. The polymer film 15 can be a biocompatible hydrophilic polymer film which exhibits some degree of dissolvability upon contact with bodily fluids. Upon dissolution, the polymer film 15 releases the odor control and/or skin wellness agents. In some embodiments the polymer film 15 can be formulated to dissolve immediately upon contact with the bodily fluids, and thereby immediately release the odor control and/or skin wellness agents. In other embodiments the polymer film 15 can be comprised of multiple layers in which a first layer may dissolve immediately upon contact with bodily fluids, but whereas a subsequent layer may dissolve more slowly, or not at all until additional contact with bodily fluids, such that the odor control and/or skin wellness agents are released gradually over time after the first insult. In other embodiments, the degree of dissolvability may be controllable to cause the odor control and/or skin wellness agents to be released gradually over a period of time after contact with bodily fluids.

The polymer film 15 could be developed, just for example, and not by way of limitation, from glycerine/polyvinyl alcohol and/or poly alkylene oxide co-polymers or other co-polymers. The odor control agents can be various types of odor eliminating agents, and can also include fragrances (or scents). In this context, the terms "fragrance" and "scent" are used interchangeably, and are considered to generally encompass the same class of substances. The skin wellness agents can comprise, just for example, and not by way of limitation, pH regulating agents, anti-fungal agents, anti-bacterial agents, anti-viral agents, anti-itch agents, an anti-inflammatory agents, lubricants, deodorants, and/or antiperspirants.

In some embodiments, such as adult incontinence garments, it can be desirable that the disposable absorbent article 10 be substantially undetectable when worn. Consequently, in such an embodiment, the polymer film 15 can be designed not to exhibit any substantially detectable scent (or fragrance), either before or after the polymer film 15 has been contacted by bodily fluids. Thus, the polymer film 15 can have substantially no scent before contact with bodily fluids. Additionally, the odor control agents released after contact with bodily fluids can be such as to eliminate odor without also releasing any type of noticeable scent (or fragrance).

Figure 3:
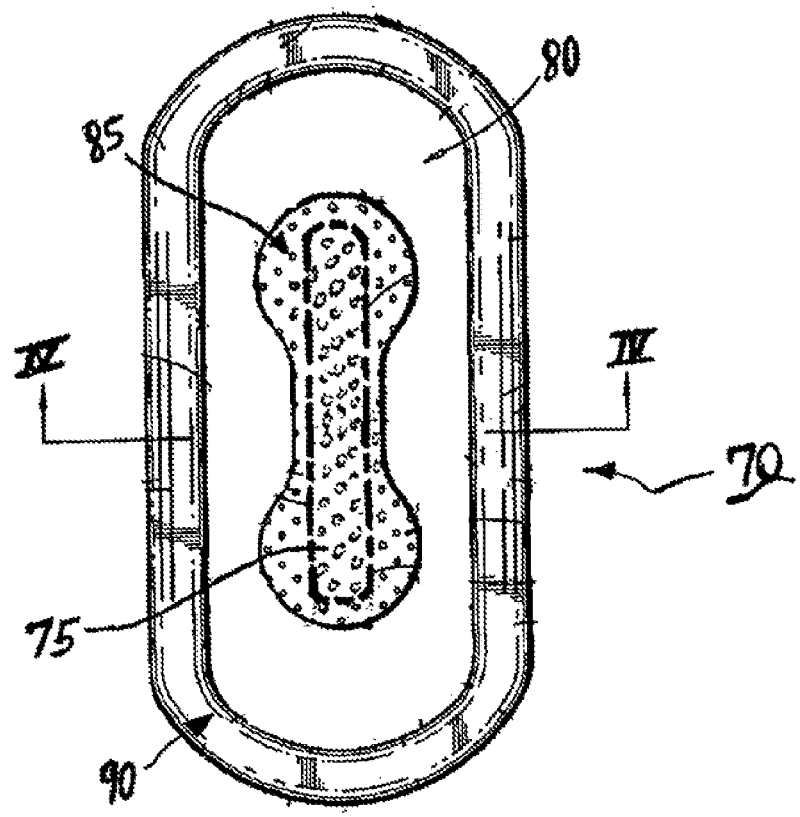
FIG. 3 is a top plan view of another embodiment of a disposable absorbent article and polymer film having odor control and/or skin wellness agents.

Turning now to FIG. 3, a further embodiment of a disposable absorbent article 70 and polymer film 75 having odor control and/or skin wellness agents is illustrated in a top plan view. As shown, the disposable absorbent article 70 can be of another conventional type, such as which can be employed with, or used as, for example, diapers, adult incontinent pads, feminine pads, sanitary napkins, pantiliners, incontinent garments, and the like. The particular disposable absorbent article 70 illustrated can generally comprise an absorbent core 80 which can further include an absorbent pledget 85.

Figure 4:
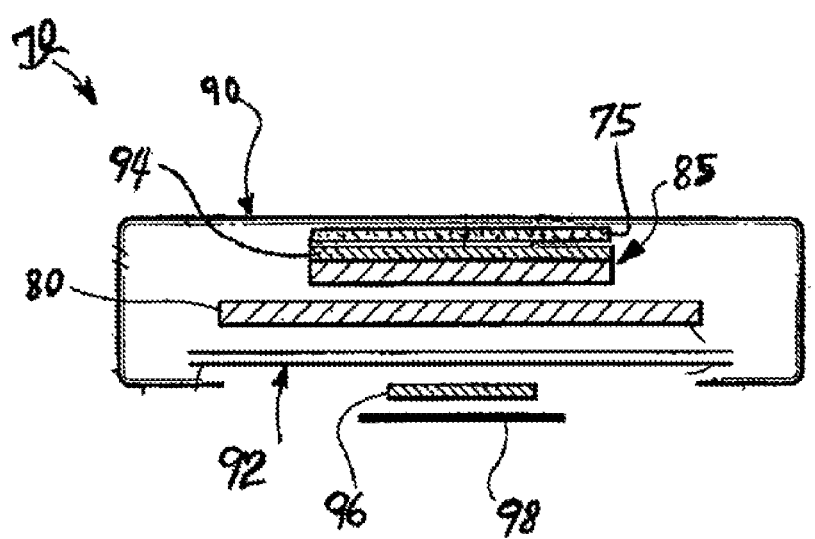
FIG. 4 is a cross section view taken along line IV-IV in FIG. 3.

Further details of the disposable absorbent article 70 are illustrated in FIG. 4, which is a cross section view taken along line IV-IV in FIG. 3. As shown, the disposable absorbent article 70 can further comprise a top sheet 90 and a back sheet 92, between which the absorbent core 80 is conventionally disposed. Additional components of the disposable absorbent article 70 can comprise a fluid acquisition layer 94, which can be positioned between the absorbent pledget 85 and the top sheet 90. Further components can include an adhesive layer 96 and an operably associated adhesive layer cover strip 98, both of which can be disposed between the back sheet 92 and, for example, a garment to which the disposable absorbent article 70 can be designed to be adhered to if/when utilized therewith.

In FIGS. 2 and 3 the polymer film 75 is shown positioned between the fluid acquisition layer 94 and the top sheet 90. However, as with the previous embodiment of the disposable absorbent article 10, the polymer film 75 could alternatively be positioned variously with respect to any of the aforesaid components of the disposable absorbent article 70. For example, the polymer film 75 could instead be positioned on the top sheet 90, between the fluid acquisition layer 94 and the absorbent pledget 85, or between the absorbent pledget 85 and the absorbent core 80. Additionally, the polymer film 75 could alternatively be positioned between the absorbent core 80 and the back sheet 92.

Although not shown, a cover sheet for the polymer film 75, such as the cover sheet 16 shown in FIG. 2, and described in connection therewith, could also be utilized with the polymer film 75 associated with the disposable absorbent article 70. Such a cover sheet may be desired if the polymer film 75 where to be positioned on the top sheet 90, where it would directly contact the skin, for the same reasons explained previously.

Figure 5A:
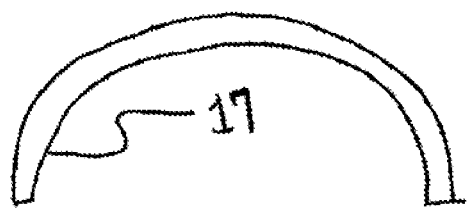
FIGS. 5A-5D illustrate various different configurations in which the polymer film having odor control and/or skin wellness agents may be produced.
Figure 5B:
Figure 5D:
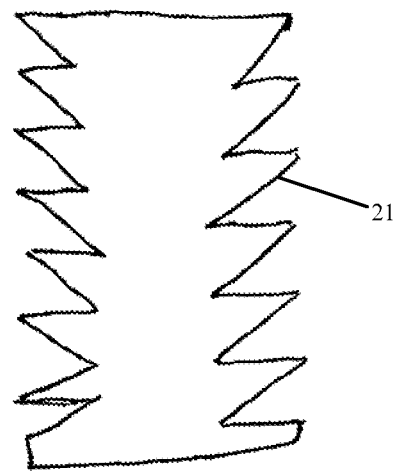
Figure 5C:
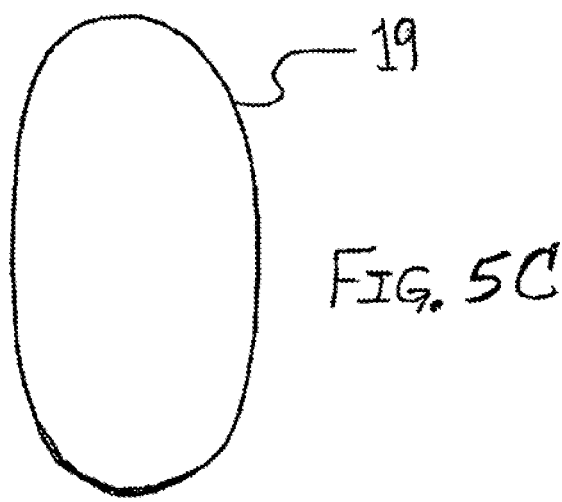

Referring now to FIGS. 5A-5D, there are illustrated various different configurations in which the polymer film 15 may be produced depending upon the intended use. For example, FIGS. 5A and 5B show the polymer film 15 produced in the form of an arcuate shaped member 17 and a thin strip 18, respectively. The arcuate shaped member 17 would facilitate applying the polymer film 15 to the leg cuffs 40, 45 of the disposable absorbent article 10, whereas the thin strip 18 would facilitate applying the polymer film 15 to either the tummy band 25 or the leg gathers 38, 40. FIGS. 5C and 5D, respectively, show the polymer film 15 produced in an oval shape 19 and a generally rectangular shape with saw tooth edges 21. In addition to the different shapes, the polymer film 15 can also be textured to increase the surface area.

Moreover, as shown in FIG. 2 and described in connection therewith, the cover sheet 16 could likewise be utilized with any of the different shaped embodiments of the polymer film illustrated in FIGS. 5A-5D, if the polymer film were positioned in contact with the skin, for the same reasons explained previously.

In another embodiment, the polymer film 15 comprising at least one of odor control and skin wellness agents could be produced as a separate article which could be adapted for attachment, such as by an appropriate adhesive, to some portion of a disposable absorbent article 10. In such an embodiment, individual articles, e.g., sheets, of the polymer film 15 of an appropriate size and configuration can be produced and sold separately, for intended use with different types of disposable absorbent articles which could be purchased separately. Alternatively, such individual sheets could be sold in combination with certain disposable absorbent articles 10.

In a further embodiment, individual such sheets of polymer film 15 could be designed to be adhered directly to the skin of the user. In such an embodiment, the polymer film 15 could be utilized separately from the disposable absorbent articles 10 with which it would normally be associated. One such application, for example, could be use of the polymer film 15 as an underarm deodorant and/or antiperspirant. In this case, the oval shaped polymer film article 19, just as an example, could be applied directly to the underarm area using a skin-appropriate adhesive. The odor control agents could be released upon contact with sweat, and the release could be immediate, gradual, or a combination thereof, in the same manner as described previously. Another such application, for example, could be to use the polymer film for shoe inserts, such as to apply odor control and/or skin wellness agents to a person's feet.

Figure 6:
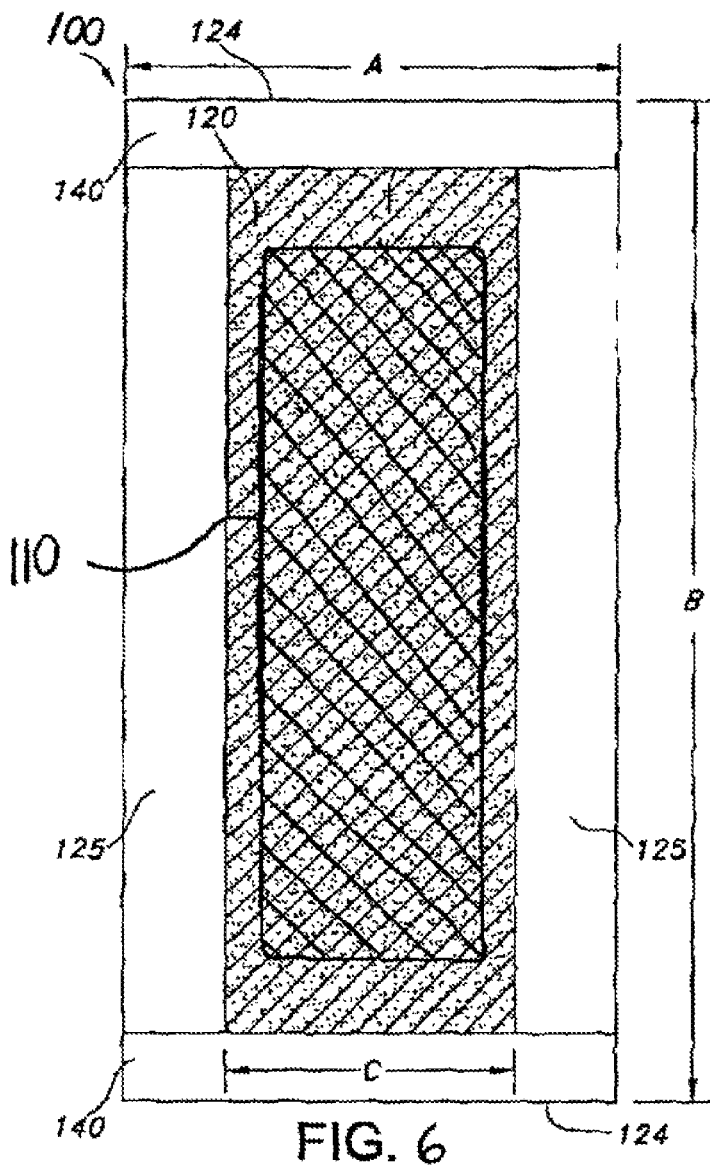
FIG. 6 is a bottom view of an embodiment of an absorbent cleaning pad and polymer film for household cleaning applications.
Figure 7:
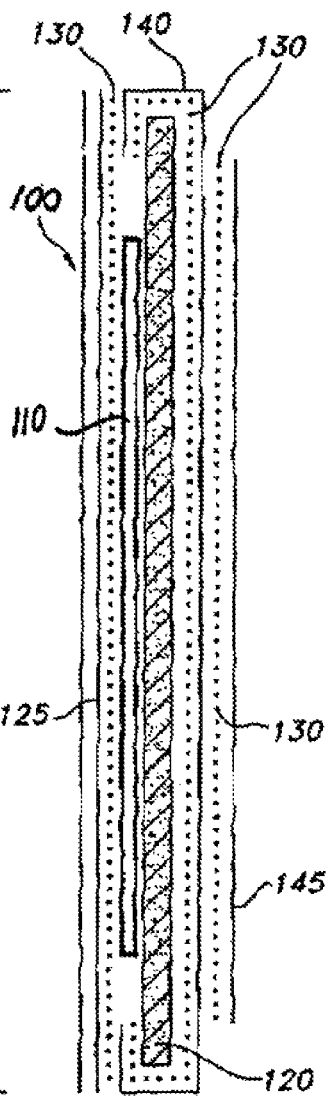
FIG. 7 is a right side view of the absorbent cleaning pad illustrated in FIG. 6.
Figure 8:
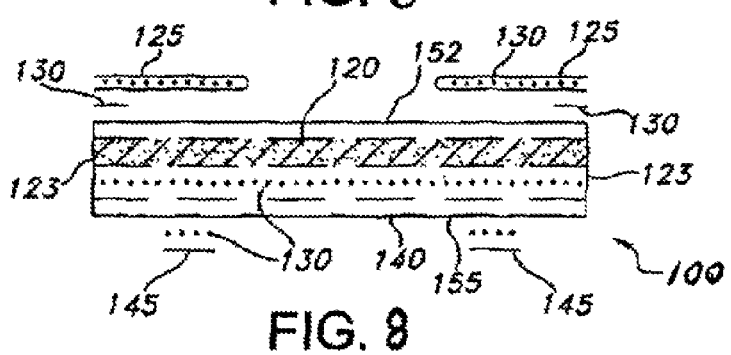
FIG. 8 is an end view of the absorbent cleaning pad illustrated in FIG. 6.

FIGS. 6-8 illustrate a particular embodiment of an absorbent cleaning pad 100 with polymer film 110 for household cleaning applications is illustrated. An example of an Absorbent Cleaning Pad Having A Durable Cleaning Surface And Method of Making Same is disclosed in U.S. patent application Ser. No. 11/240,929, filed Sep. 30, 2005, assigned to the assignee of the present invention, which is hereby incorporated herein by reference. As shown in the figures, the absorbent cleaning pad 100 with polymer film 110 can further generally comprise a unitized airlaid composite 120, supplementary dirt entrapment surfaces in the form of two lofty cuffs 125, a backing layer 140, and two attachment members 145. Each lofty cuff 125 can be folded into two equal segments and positioned along the length "B" of the unitized airlaid composite 120, although each cuff can alternatively be formed from a single layer of material. A portion of the width of each lofty cuff 125 can be bonded to a cleaning surface or side 152 of the unitized airlaid composite 120 using an adhesive 130. The backing layer 140 can be adhered to the attachment surface or side 155 of the unitized airlaid composite 120, such as via an adhesive 130, and folded around the width-wise sides 124 of the unitized airlaid composite 120, thereby enclosing the width-wise sides 124. The backing layer 140 is optionally eliminated, and the function of the backing layer 140 can alternatively be eliminated or provided by applying an agent directly to a surface or a surface portion of the pad body or by otherwise chemically, mechanically, or thermally modifying the surface of the pad body.

The polymer film 110 can comprise various well known household cleaning agents which suitable for cleaning bathrooms, kitchens, showers, glass, wood, tile, and the like. Although the polymer film 110 is illustrated on the cleaning surface or side 152, it could alternatively be provided in other positions, such as, for example, between the airlaid composite 120 and the backing layer 140. As described previously, the polymer film 110 can similarly be formulated to release household cleaning agents immediately, gradually over a period of time after contact with water, or a combination thereof. The polymer film 110 can be a hydrophilic polymer film which exhibits some degree of dissolvability upon contact with water. Upon dissolution, the polymer film 110 releases the household cleaning agents. In some embodiments the polymer film 110 can be formulated to dissolve immediately upon contact with water, and thereby immediately release the household cleaning agents. In other embodiments the polymer film 110 can be comprised of multiple layers in which a first layer may dissolve immediately upon contact with water, but whereas a subsequent layer may dissolve more slowly, or not at all until additional contact with water, such that the household cleaning agents are released gradually over time after the first exposure to water. In other embodiments, the degree of dissolvability may be controllable to cause the household cleaning agents to be released gradually over a period of time after contact with water.

What has been described above includes exemplary embodiments of a disposable absorbent article 10 and polymer film 15, the polymer film 15 alone, having odor control and/or skin wellness agents, and an absorbent cleaning pad with polymer film 110 for household cleaning applications. It is, of course, not possible to describe every conceivable combination of components or methodologies for purposes of this description, but one of ordinary skill in the art may recognize that further combinations and permutations are possible in light of the overall teaching of this disclosure. Accordingly, the description provided herein is intended to be illustrative only, and should be considered to embrace any and all alterations, modifications, and/or variations that fall within the spirit and scope of the appended claims. Furthermore, to the extent that the term "includes" may be used in either the detailed description or elsewhere, the use of this term is intended to be inclusive in a manner similar to the term "comprising" as that term is interpreted as a transitional word in a claim.

What is claimed is:

1. A disposable absorbent article comprising a polymer film positioned to be activated by contact with bodily fluids, said polymer film releasing odor control and skin wellness agents upon contact with said bodily fluids, said polymer film is comprised of multiple layers to implement a gradual release of said odor control and skin wellness agents over time.

2. The disposable absorbent article of claim 1 wherein said polymer film is a biocompatible hydrophilic polymer film.

3. The disposable absorbent article of claim 1 wherein said polymer film releases said odor control and skin wellness agents gradually over a period of time after contact with said bodily fluids.

4. The disposable absorbent article of claim 3 wherein said polymer film exhibits some degree of dissolvability upon contact with said bodily fluids.

5. The disposable absorbent article of claim 4 wherein said degree of dissolvability is controllable to cause said odor control and skin wellness agents to be released gradually over a period of time after contact with said bodily fluids.

6. The disposable absorbent article of claim 1 further comprising a top sheet, a back sheet, and an absorbent core disposed therebetween, and wherein said polymer film is positioned on the top sheet.

7. The disposable absorbent article of claim 1 further comprising a top sheet, a back sheet, and an absorbent core disposed therebetween, and wherein said polymer film is positioned between the top sheet and the absorbent core.

8. The disposable absorbent article of claim 1 further comprising a top sheet, a back sheet, and an absorbent core disposed therebetween, and wherein said polymer film is positioned between the back sheet and the absorbent core.

9. The disposable absorbent article of claim 1 further comprising a top sheet, a back sheet, and an absorbent core disposed therebetween, said absorbent core further comprising a core wrap and a fluid acquisition layer between the core wrap and the top sheet, and wherein said polymer film is positioned between the top sheet and the fluid acquisition layer.

10. The disposable absorbent article of claim 1 further comprising a top sheet, a back sheet, and an absorbent core disposed therebetween, said absorbent core further comprising a core wrap surrounding the core and a fluid acquisition layer between the core wrap and the top sheet, and wherein said polymer film is positioned between the fluid acquisition layer and the core wrap.

11. The disposable absorbent article of claim 1 further comprising a top sheet, a back sheet, and an absorbent core disposed therebetween, said absorbent core further comprising a core wrap surrounding the core, and a fluid acquisition layer between the core wrap and the top sheet, and wherein said polymer film is positioned within the core wrap.

12. The disposable absorbent article of claim 1 further comprising a top sheet, a back sheet, and an absorbent core disposed therebetween, said absorbent core further comprising a core wrap surrounding the core, and a fluid acquisition layer between the core wrap and the top sheet, and wherein said polymer film is positioned within the core itself.

13. The disposable absorbent article of claim 1 further comprising further comprising a top sheet, a back sheet, an absorbent core disposed therebetween, and at least one of leg cuffs, a tummy band, and side panels, and wherein said polymer film is associated with at least one of said leg cuffs, tummy band, and side panels.

14. The disposable absorbent article of claim 1 wherein said odor control agents comprise at least one of odor eliminating agents and fragrances.

15. The disposable absorbent article of claim 1 wherein said skin wellness agents comprise at least one of a pH regulating agent, anti-fungal agent, anti-bacterial agent, anti-viral agent, anti-itch agent, anti-inflammatory agent, lubricant, and deodorant.

16. The disposable absorbent article of claim 1 wherein said polymer film has substantially no detectable scent at least one of before and after being contacted by said bodily fluids.

17. The disposable absorbent article of claim 1 further comprising a cover sheet covering at least a portion of said polymer film.

18. A polymer film comprising odor control and skin wellness agents, said polymer film releasing said odor control and skin wellness agents upon contact with bodily fluids, said polymer film adapted to be at least one of attached to a portion of a disposable absorbent article disposed adjacent the skin of the user, wherein said polymer film is comprised of multiple layers to implement a gradual release of said odor control and skin wellness agents over time.

19. The polymer film of claim 18 wherein said polymer film is a biocompatible hydrophilic polymer film.

20. The polymer film of claim 19 wherein said polymer film releases said odor control and skin wellness agents gradually over a period of time after contact with said bodily fluids.

21. The polymer film of claim 20 wherein said polymer film exhibits some degree of dissolvability upon contact with said bodily fluids.

22. The polymer film of claim 21 wherein said degree of dissolvability is controllable to cause said odor control and skin wellness agents to be released gradually over a period of time after contact with said bodily fluids.

23. The polymer film of claim 18 wherein said odor control agents comprise at least one of odor eliminating agents and fragrances.

24. The polymer film of claim 18 wherein said skin wellness agents comprise at least one of a pH regulating agent, anti-fungal agent, anti-bacterial agent, anti-viral agent, anti-itch agent, anti-inflammatory agent, lubricant, and deodorant.

25. The polymer film of claim 18 wherein said polymer film has substantially no detectable scent at least one of before and after being contacted by said bodily fluids.

26. The polymer film of claim 18 wherein said polymer film is adapted to adhere to the underarm area of a user, said polymer film releases said odor control agent, and said bodily fluid is sweat.

27. The polymer film of claim 26 wherein said odor control agents are at least one of a deodorant and an antiperspirant.

28. The polymer film of claim 26 wherein said polymer film releases said odor control agents gradually over a period of time after contact with sweat.

29. The disposable absorbent article of claim 18 further comprising a cover sheet covering at least a portion of said polymer film.

* * * * *